United States Patent [19]

Schaper et al.

[11] 4,338,089

[45] Jul. 6, 1982

[54] PROCESS FOR PREPARATION OF HYDROCARBONS

[75] Inventors: Lambert Schaper; Swan T. Sie, both of Amsterdam, Netherlands

[73] Assignee: Shell Oil Company, Houston, Tex.

[21] Appl. No.: 174,066

[22] Filed: Jul. 31, 1980

[30] Foreign Application Priority Data

Aug. 6, 1979 [NL] Netherlands .......................... 7906003

[51] Int. Cl.$^3$ .............................................. C07C 1/04
[52] U.S. Cl. .................................... 518/707; 518/708; 518/728; 518/716; 518/714; 518/713; 252/455 Z
[58] Field of Search ................ 518/706, 707, 708, 728

[56] References Cited

U.S. PATENT DOCUMENTS

| | | | |
|---|---|---|---|
| 1,741,308 | 12/1929 | Jaeger | 518/706 |
| 2,527,154 | 10/1950 | Scharmaan | 260/449.6 |
| 2,560,344 | 7/1951 | Hemminger | 518/708 |
| 2,651,653 | 9/1953 | Hemminger | 260/449.6 |
| 3,845,150 | 10/1974 | Yan et al. | 518/728 |
| 4,046,830 | 9/1977 | Kuo | 208/88 |
| 4,086,262 | 4/1978 | Chang et al. | 260/449.6 |
| 4,096,163 | 6/1978 | Chang et al. | 260/449 |
| 4,159,995 | 7/1979 | Haag et al. | 585/322 |

FOREIGN PATENT DOCUMENTS 7711719 5/1979 Netherlands .
2006819 5/1979 United Kingdom .

*Primary Examiner*—Bernard Helfin
*Attorney, Agent, or Firm*—John M. Duncan; Ronald R. Reper

[57] ABSTRACT

A process is disclosed for the preparation of a hydrocarbon mixture by contacting in a first stage a feed mixture of hydrogen and carbon monoxide with an $H_2/CO$ molar ratio of less than 1.0 with a trifunctional catalyst combination containing (a) at least one metal component having catalytic activity for conversions of a $H_2/CO$ mixture into acyclic hydrocarbons, and/or acyclic oxygen-containing hydrocarbons, (b) at least one metal component for the conversion of an $H_2O/CO$ mixture into an $H_2/CO$ mixture, and (c) a certain crystalline silicate containing at least one trivalent metal selected from aluminum, iron, gallium, rhodium, chromium and scandium, wherein the molar ratio of the trivalent metal oxide to silica is less than 0.1; adjusting the $H_2/CO$ molar to at least 1.5 by adding $H_2O$, if necessary; followed by contacting in a second stage at least the $C_2$- fraction of the reaction product from the first stage with a bifunctional catalyst combination containing at least one metal component with catalytic activity for converting an $H_2/CO$ mixture into acyclic hydrocarbons and also at least one metal component with catalytic activity for converting an $H_2O/CO$ mixture into an $H_2/CO_2$ mixture.

15 Claims, No Drawings

PROCESS FOR PREPARATION OF HYDROCARBONS

BACKGROUND OF THE INVENTION

The invention relates to a process for the preparation of a hydrocarbon mixture from a mixture of carbon monoxide and hydrogen with an $H_2/CO$ molar ratio of less than 1.0, using a trifunctional catalyst combination containing one or more metal components with catalytic activity for the conversion of an $H_2/CO$ mixture into acyclic hydrocarbons and/or acyclic oxygen-containing hydrocarbons, one or more metal components with catalytic activity for the conversion of an $H_2O/CO$ mixture into an $H_2/CO_2$ mixture and a crystalline silicate having the capability of catalyzing the conversion of acyclic hydrocarbons and acyclic oxygen-containing hydrocarbons into aromatic hydrocarbons. The said crystalline silicates are characterized in that they have the following properties:

(a) thermally stable up to a temperature about 600° C., (b) an X-ray powder diffraction pattern showing, inter alia, the reflections given in Table A.

TABLE A

| Radiation: Cu - Kα 2 θ | Wavelength 0.15418 nm relative intensity |
|---|---|
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | wherein the letters used have the following meanings: VS=very strong; S=strong; M=moderate; W=weak; θ=angle according to Bragg.

(c) in the formula which represents the composition of the silicate, expressed in moles of the oxides, and in which, in addition to oxides of hydrogen, alkali metal and/or alkaline-earth metal and silicon, there is present one or more oxides of a trivalent metal A selected from the group formed by aluminum, iron, gallium, rhodium, chromium and scandium, the $A_2O_3/SiO_2$ molar ratio (for the sake of brevity further designated m in this patent application) is less than 0.1. In an investigation by the Applicant concerning this process it was found that it has two drawbacks. In the first place, when using space velocities acceptable in actual practice, the conversion of the $H_2/CO$ mixture is found to be unsatisfactory. Further, the process yields a product substantially consisting of hydrocarbons with at most 12 carbon atoms in the molecule and only very few hydrocarbons with more than 12 carbon atoms in the molecule.

Further investigation by the Applicant concerning this process has shown that the two above-mentioned drawbacks can be obviated by giving the reaction product, or at least its $C_2^-$ fraction, an after-treatment by contacting it with a catalyst containing one or more metal components with catalytic activity for the conversion of an $H_2/CO$ mixture into acyclic hydrocarbons, which metal components have been selected from the group formed by Ni, Co and Ru, on the understanding that if the feed for the second step has an $H_2/CO$ molar ratio of less than 1.5, water is added to this feed and that in the second step a bifunctional catalyst combination is used, which contains, in addition to metal components with catalytic activity for the conversion of an $H_2/CO$ mixture into acyclic hydrocarbons, also one or more metal components with catalytic activity for the conversion of an $H_2O/CO$ mixture into an $H_2/CO_2$ mixture. In this way it is achieved that, when using space velocities acceptable in actual practice, not only a very high conversion of the $H_2/CO$ mixture is obtained, but also that the reaction product consists substantially of hydrocarbons with more than 12 carbon atoms in the molecule.

SUMMARY OF THE INVENTION

The present patent application therefore relates to a process for the preparation of a hydrocarbon mixture, from a feed mixture of carbon monoxide and hydrogen with an $H_2/CO$ molar ratio of less than 1.0 which comprises contacting said feed at an elevated temperature and pressure in a first step with a trifunctional catalyst combination containing: (a) at least one metal component with catalytic activity for the conversion of an $H_2/CO$ mixture into acyclic hydrocarbons and/or acyclic oxygen-containing hydrocarbons, (b) at least one metal component with catalytic activity for the conversion of an $H_2O/CO$ mixture into an $H_2/CO_2$ mixture, and (c) a crystalline silicate, which silicate has the following properties:

(a) thermally stable up to a temperature above 600° C., (b) an X-ray powder diffraction pattern showing, inter alia, the reflections given in Table A of the specification, (c) a composition which includes oxides of hydrogen, alkali metal and/or alkaline-earth metal and silicon, and at least one oxide of a trivalent metal, A, selection from the group formed by aluminum, iron, gallium, rhodium, chromium and scandium, wherein the $A_2O_3/SiO_2$ molar ratio(m) is less than 0.1; and contacting at least the $C_2^-$ fraction of the reaction product from the first contact zone in a second contact zone at an elevated temperature and pressure with a catalyst containing at least one metal component with catalytic activity for the converstion of an $H_2/CO$ mixture into acyclic hydrocarbons, which metal components have been selected from the group formed by cobalt, nickel and ruthenium, with the proviso that (a) if the feed in the second contact zone has an $H_2/CO$ molar ratio of less than 1.5, water is added to this feed, and (b) that said second contact zone contains a bifunctional catalyst combination which includes both said metal component with catalytic activity for the conversion of an $H_2/CO$ mixture into acyclic hydrocarbons, and at least one metal component with catalytic activity for the conversion of an $H_2O/CO$ mixture into an $H_2/CO_2$ mixture.

DESCRIPTION OF PREFERRED EMBODIMENTS

In the process according to the invention the starting material is an $H_2/CO$ mixture with an $H_2/CO$ molar ratio of less than 1.0. Such $H_2/CO$ mixtures can very suitably be prepared by steam gasification of a carbon-containing material. Examples of such materials are brown coal, anthracite, coke, crude mineral oil and fractions thereof and oils extrated from tar sand and bituminous shale. The steam gasification is preferably carried out at a temperature of 900°–1500° C. and a pressure of 10–100 bar. In the process according to the invention it is preferred to start from an $H_2/CO$ mixture with an $H_2/CO$ mixture with an $h_2/CO$ molar ratio of more than 0.25.

The trifunctional catalyst combinations used in the process according to the invention in the first step contain, in addition to the metal components with catalytic activity, a crystalline metal silicate characterized by the properties mentioned under (a)–(c). Although, in principle the silicates may contain several metals selected from the group formed by aluminum, iron, gallium, rhodium, chromium and scandium, is is preferred for the process according to the invention to use catalysts in which the silicate contains only one of these metals and in particular silicates which contain as the metal aluminum, iron or gallium. As regards the presence of aluminum in the silicates, the following remarks should be made. The silicon compounds, which from an economic point of view are suitable for the preparation of crystalline silicates on a technical scale, contain as a rule a small amount of aluminum as contaminant. Usually, this aluminum is found, at least partly, in the silicate prepared. This means that, if the aim is to prepare for use in the trifunctional catalyst combinations a crystalline silicate containing one or more of the metals iron, gallium, rhodium, chromium and scandium, while the starting material is a base mixture in which a silicon compound contaminated with aluminum has been incorporated, as a rule a crystalline silicate will be obtained containing a slight amount of aluminum.

The crystalline silicates used in the trifunctional catalyst combinations should have a value for m which is less than 0.1. It is preferred to use crystalline silicates for which m is greater than 0.001 and particularly greater than 0.002 and silicates for which m is smaller than 0.05. If in the process according to the invention use is made of a trifunctional catalyst combination in which a crystalline aluminum silicate is present for which m is greater than 0.005, it is preferred to choose for this purpose an aluminum silicate which contains 0.1–10%w of one of the elements selected from the group formed by manganese, calcium, magnesium and titanium and particularly manganese.

The crystalline silicate used in the trifunctional catalyst combinations has been defined, inter alia, with reference to the X-ray powder diffraction pattern. This X-ray powder diffraction pattern should contain, inter alia, the reflections shown in Table A. The complete X-ray powder diffraction pattern of a typical example of a silicate suitable for use according to the invention is shown in Table B. (Radiation: Cu—Kα; wavelength: 0.15418 nm).

TABLE B

| 2 θ | relative intensity (100. $I/I_o$) | description |
|---|---|---|
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |
| 15.95 | 9 | BD |

TABLE B-continued

| 2 θ | relative intensity (100. $I/I_o$) | description |
|---|---|---|
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100ˣ | SP |
| 23.95 | 45 | SP |
| 24.40 | 27 | SP |
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

ˣ$I_o$ = intensity of the strongest separate reflection present in the pattern.

The letters used in Table B for describing the reflections have the following meanings: SP=sharp; SR=shoulder; NL=normal; BD=broad; θ=angle according to Bragg.

The crystalline silicates used in the trifunctional catalyst combinations can be prepared starting from an aqueous mixture containing the following compounds: one or more compounds of an alkali metal or alkaline-earth metal (M), one or more compounds containing an organic cation (R) or from which such a cation is formed during the preparation of the silicate, one or more silicon compounds and one or more compounds in which a trivalent metal A selected from the group formed by aluminum, iron, gallium, rhodium, chromium and scandium is present. The preparation is performed by maintaining the mixture at elevated temperature until the silicate has been formed and subsequently separating the crystals of the silicate from the mother liquor and calcining them. In the aqueous mixture from which the silicates are prepared the various compounds should be present in the following ratio, expressed in moles of the oxides:

$M_{2/n}O: R_2O = 0.1-20$, $R_2O: SiO_2 = 0.01-0.5$, $SiO_2: A_2O_3 > 10$, and $H_2O: SiO_2 = 5-50$; (n is the valency of M)

In the preparation of the silicates it is preferred to start from a base mixture in which M is present in an alkali metal compound and R in a tetra-alkylammonium compound and in particular from a base mixture in which M is present in a sodium compound and R in a tetrapropylammonium compound. The crystalline silicates prepared as described above contain alkali metal ions and/or alkaline-earth metal ions. They can be replaced by other cations such as hydrogen ions or ammonium ions by using suitable exchange methods. The crystalline silicates used in the trifunctional catalyst combinations preferably have an alkali metal content of less than 0.1%w and in particular less than 0.05%w.

The trifunctional catalyst combinations used in the first contact zone or first step of the process according to the invention contain one or more metal components with catalytic activity for the conversion of an $H_2/CO$ mixture into acyclic hydrocarbons and/or acyclic oxygen-containing hydrocarbons, one or more metal components with catalytic activity for the conversion of an $H_2O/CO$ mixture into an $H_2/CO_2$ mixture, and a crystalline silicate as defined hereinbefore with catalytic activity for the conversion of acyclic hydrocarbons and acyclic oxygen-containing hydrocarbons into aromatic hydrocarbons. The ratio in which the three catalytic functions are present in the catalyst combination may vary within wide limits and is chiefly determined by the activity of each of the catalytic functions. It is intended that in the first step of the process according to the invention as much as possible of the acyclic hydrocarbons and/or acyclic oxygen-containing hydrocarbons formed under the influence of a first catalytic function, are converted into aromatic hydrocarbons under the influence of a second catalytic function, while of the water liberated in the conversion of the $H_2/CO$ mixture into hydrocarbons and/or in the conversion of oxygen-containing hydrocarbons into aromatic hydrocarbons, and of the water that was optionally added to the feed, as much as possible reacts with the excess amount of CO present in the $H_2/CO$ mixture under the influence of a third catalytic function, with formation of an $H_2/CO_2$ mixture.

Although the trifunctional catalyst combinations are described in this patent application as catalyst combinations containing one or more metal components with catalytic activity for the conversion of an $H_2/CO$ mixture into acyclic hydrocarbons and/or acyclic oxygen-containing hydrocarbons and one or more metal components with catalytic activity for the conversion of an $H_2O/CO$ mixture into an $H_2/CO_2$ mixture, this does not mean at all that separate metal components that each have one of the two catalytic functions should always be present in the catalyst combinations. For, it has been found that metal components and combinations of metal components with catalytic activity for the conversion of an $H_2/CO$ mixture into substantially acyclic oxygen-containing hydrocarbons often also have sufficient catalytic activity for the conversion of an $H_2O/CO$ mixture into an $H_2/CO_2$ mixture, so that incorporation of one metal component or one combination of metal components into the catalyst combinations will then usually suffice. Metal components and combinations of metal components with catalytic activity for the conversion of an $H_2/CO$ mixture into substantially acyclic hydrocarbons, usually have no or insufficient activity for the conversion of an $H_2O/CO$ mixture into an $H_2/CO_2$ mixture. When using such metal components or combinations of metal components in the trifunctional catalyst combinations, one or more separate metal components with catalytic activity for the conversion of an $H_2O/CO$ mixture into an $H_2/CO_2$ mixture should therefore in most cases be incorporated into these metal components.

The trifunctional catalyst combinations used in the first step of the process according to the invention are preferably composed of two or three separate catalysts, which will, for convenience, be designated catalysts X, Y and Z. Catalyst X is the one containing the metal components having catalytic activity for the conversion of an $H_2/CO$ mixture into acyclic hydrocarbons and/or acyclic oxygen-containing hydrocarbons. Catalyst Y is the crystalline silicate. Catalyst Z is the one containing the metal components having catalytic activity for the conversion of an $H_2O/CO$ mixture into an $H_2/CO_2$ mixture. As has been explained hereinbefore the use of a Z-catalyst may be omitted in some cases.

If as the X-catalyst a catalyst is used which is capable of converting an $H_2/CO$ mixture into substantially acyclic oxygen-containing hydrocarbons, preference is given to a catalyst which is capable of converting the $H_2/CO$ mixture into substantially methanol and/or dimethyl ether. Very suitable catalysts for this purpose are $ZnO-Cr_2O_3$ compositions, in particular such compositions in which the atomic percentage of zinc, based on the sum of zinc and chromium, is at least 60% and preferably 60–80%. When using a $ZnO-Cr_2O_3$ composition as X-catalyst, the use of a Z-catalyst may be omitted.

X-catalysts which are capable of converting an $H_2/CO$ mixture into substantially acyclic hydrocarbons are referred to in the literature as Fischer-Tropsch catalysts. Such catalysts contain one or more metals from the iron group or ruthenium together with one or more promotors to increase the activity and/or selectivity and sometimes a carrier material such as kieselguhr. If in the first step of the process according to the invention use is made of a trifunctional catalyst combination in which the X-catalyst is a Fischer-Tropsch catalyst, it is preferred to choose for this purpose an iron or cobalt catalyst, in particular such a catalyst which has been prepared by impregnation. Very suitable catalysts for this purpose are:

(a) Catalysts that contain 30–75 pbw iron and 5–40 pbw magnesium for 100 pbw alumina and which have been prepared by impregnating an alumina carrier with one or more aqueous solutions of salts of iron and of magnesium followed by drying the composition, calcining it at a temperature of 700°–1200° C. and reducing it. Particular preference is given to such catalysts that contain, in addition to 40–60 pbw iron and 7.5–30 pbw magnesium, 0.5–5 pbw copper as the reduction promotor and 1–5 pbw potassium as the selectivity promotor per 100 pbw alumina, and which have been calcined at 750°–850° C. and reduced at 250°–350° C.

(b) Catalysts that contain 10–40 pbw iron and 0.25–10 pbw chromium per 100 pbw silica and which have been prepared by impregnating of silica carrier with one or more aqueous solutions of salts of iron and of chromium, followed by drying the composition, calcining it and reducing it at a temperature of 350°–750° C. Particular preference is given to such catalysts which contain, in addition to 20–35 pbw iron and 0.5–5 pbw chromium, 1–5 pbw potassium as the selectivity promotor and which have been calcined at 350°–700° C. and reduced at 350°–500° C.

(c) Catalysts that contain 10–40 pbw cobalt and 0.25–5 pbw zirconium, titanium or chromium per 100 pbw silica and which have been prepared by impregnating a silica carrier with one or more aqueous solutions of salts of cobalt and zirconium, titanium or chromium followed by drying the composition, calcining it at 350°–750° C. and reducing it at 200°–350° C.

When using the iron catalysts mentioned under (a) and (b) as X-catalyst, the use of a Z-catalyst can be omitted. When using the cobalt catalysts mentioned under (c) as X-catalyst, a Z-catalyst should also be incorporated into the trifunctional catalysts. If in the first step of the process according to the invention use is made of a trifunctional catalyst combination in which catalyst X is a Fischer-Tropsch catalyst, it is preferred to choose for this purpose an iron catalyst as described under (a) and (b).

Z-catalysts which are capable of converting an $H_2O/CO$ mixture into an $H_2/CO_2$ mixture are referred to in the literature as CO-shift catalysts. If in the first step of the process according to the invention use is made of trifunctional catalyst combination in which a Z-catalyst is present, it is preferred to use as Z-catalyst a CuO-ZnO composition, and particularly such a composition in which the Cu/Zn atomic ratio is 0.25-4.0.

In the trifunctional catalyst combinations the catalysts X, Y and, optionally, Z are preferably present as a physical mixture. When carrying out the first step of the process, using a fixed catalyst bed, this bed may also be built up of alternate layers of particles of the catalysts X, Y and, optionally, Z.

The first step of the process according to the invention can very suitably be carried out by conducting the feed in upward or in downward direction through a vertically mounted reactor in which a fixed or moving bed of the trifunctional catalyst combination is present. The first step may, for instance, be carried out in the so-called fixed-bed operation, in bunker-flow operation, in ebulated-bed operation or fluidized-bed operation. The first step of the process is preferably carried out under the following conditions: a temperature of 200°-500° C. and particularly of 250°-450° C., a pressure of 1-150 bar and particularly of 5-100 bar and a space velocity of 50-5000 and particularly of 300-3000 Nl gas/l catalyst/h.

In the process according to the invention at least the $C_2^-$ fraction of the reaction product from the first step is used as the feed for the second contact zone, i.e., the second step. Instead of the $C_2^-$ fraction of the reaction product from the first step, a different fraction of this product, e.g. the $C_4^-$ fraction, or even the whole product from the first step, may be used—if desired—as the feed for the second step. In the second step of the process according to the invention it is intended to convert as much as possible of the CO present in the feed for the second step into acyclic hydrocarbons over a monofunctional catalyst containing one or more metal components with catalytic activity for the conversion of an $H_2/CO$ mixture into acyclic hydrocarbons, which metal components have been selected from the group formed by cobalt, nickel and ruthenium. To this end the $H_2/CO$ molar ratio in the feed for the second step should be at least 1.5 and preferbly 1.75-2.25. When using an $H_2/CO$ mixture with a high $H_2/CO$ molar ratio as the feed for the first step, the process according to the invention can yield a reaction product from the first step, which has an $H_2/CO$ molar ratio of at least 1.5, which is suitable, as such, to be converted in the second step over the said catalyst. An attractive way of ensuring in the process according to the invention that the reaction product from the first step has an $H_2/CO$ molar ratio of at least 1.5 is adding water to the feed for the first sep. Under the influence of the catalyst combination present in the first step this water reacts with CO from the feed to form an $H_2/CO_2$ mixture. A further advantage of the addition of water to the feed of the first step in the process according to the invention is that it increases the stability of the catalyst combination. Water addition to the feed for the first step can be applied in the process according to the invention both in cases where without water addition the first step would have been given a reaction product with an $H_2/CO$ molar ratio of less than 1.5, and in cases where, also without water addition, the first step would have given a reaction product with an $H_2/CO$ molar ratio of at least 1.5, but where it is desirable that the feed which is contacted with the catalyst in the second step has a higher $H_2/CO$ molar ratio. If in the process according to the invention an embodiment is chosen in which water is added to the feed for the first step, the amount of water required is substantially determined by the $H_2/CO$ molar ratio of the feed for the first step, the activity of the catalyst combination in the first step for converting an $H_2O/CO$ mixture into an $H_2/CO_2$ mixture and the desired $H_2/CO$ molar ratio of the reaction product of the first step.

If in the process according to the invention a reaction product is obtained from the first step with an $H_2/Co$ molar ratio of less than 1.5, after water addition to the feed for the first step or not, water should be added to the feed for the second step and in the second step a bifunctional catalyst combination should be incorporated, which contains, in addition to the metal components with catalytic activity for the conversion of an $H_2/Co$ mixture into acyclic hydrocarbons, also one or more metal components with catalytic activity for the conversion of an $H_2O/CO$ mixture into an $H_2/CO_2$ mixture. The bifunctional catalyst combinations which are optionally used in the second step of the process according to the invention, are preferably composed of two separate catalysts, which will, for convenience, be designated catalyst A and catalyst B. Catalyst A is the one containing the metal components having catalytic activity for the conversion of an $H_2/CO$ mixture into acyclic hydrocarbons, and which metal components have been selected from the group formed by cobalt, nickel and ruthenium. Catalyst B is the one containing the metal components having catalytic activity for the conversion of an $H_2O/CO$ mixture into an $H_2/CO_2$ mixture. Both when using a monofunctional catalyst and when using a bifunctional catalyst combination in the second step of the process according to the invention, preference is given to a cobalt catalyst as the A-catalyst and in particular to a cobalt catalyst prepared by impregnation. Very suitable catalysts for this purpose are the cobalt catalysts described hereinbefore under (c). Suitable B-catalysts are the usual CO-shift catalysts. Just as for catalyst Z, which should optionally be used in the first step of the process, it also holds for catalyst B that preference is given to a CuO-ZnO composition, and in particular such a composition in which the Cu/Zn atomic ratio lies between 0.25 and 4.0. In the bifunctional catalyst combinations catalysts A and B may be present as a physical mixture. When the second step of the process is carried out using a fixed catalyst bed, this bed is preferably built up of two or more alternate layers of particles of, successively, catalyst B and catalyst A. Water addition to the feed for the second step together with the use of a bifunctional catalyst combination in the second step can be used in the process according to the invention both in cases where the reaction product from the first step has an $H_2/CO$ molar ratio of less than 1.5, and in cases where the reaction product from the first step already has an $H_2/CO$ molar ratio of at least 1.5, but where it is desirable that the feed which is contacted with catalyst A in the second step should have a higher $H_2/CO$ molar ratio. If in the process according to the invention an embodiment is chosen in which water is added to the feed for the second step together with the use of a bifunctional catalyst combination in the second step, the amount of water required is substantially determined by the $H_2/CO$ molar ratio of the feed for the second step, the activity of the catalyst combination for the conversion of an $H_2O/CO$ mixture into an $H_2/CO_2$ mixture and the desired $H_2/CO$ molar ratio of the product that is contacted with catalyst A.

The second step of the process according to the invention can very conveniently be carried out by conducting the feed in upward or in downward direction through a vertically mounted reactor in which a fixed bed of the monofunctional catalyst or of the bifunctional catalyst combination is present. The second step of the process can also be carried out using a suspension of the catalyst or catalyst combination in a hydrocarbon oil. The second step of the process is preferably carried out under the following conditions: a temperature of 125°–350° C. and in particular of 175°–275° C. and a pressure of 1–150 bar and in particular 5–100 bar.

The invention will now be explained with reference to the following example:

EXAMPLE

The following catalysts were used in the investigation:

CATALYST 1

A $Co/Zr/SiO_2$ catalyst that contained 25 pbw cobalt and 1.8 pbw zirconium per 100 pbw silica and which had been prepared by impregnating a silica carrier with an aqueous solution containing a cobalt and a zirconium salt, followed by drying the composition, calcining it at 500° C. and reducing it at 280° C.

CATALYST 2

An $Fe/Mg/Cu/K/Al_2O_3$ catalyst that contained 50 pbw iron, 20 pbw magnesium, 2.5 pbw copper and 4 pbw potassium per 100 pbw alumina and which had been prepared by impregnating an alumina carrier with an aqueous solution containing an iron, a magnesium, a copper and a potassium salt, followed by drying the composition, calcining it at 800° C. and reducing it at 325° C.

CATALYST 3

A $Cu/Zn/Al_2O_3$ catalyst with a Cu/Zn atomic ratio of 0.55.

CATALYST 4

A $ZnO-Cr_2O_3$ catalyst in which the atomic percentage of zinc based on the sum of zinc and chromium was 70%.

CATALYST 5-7

Three crystalline silicates (silicates A-C) were prepared by heating mixtures of $SiO_2$, NaOH, $[(C_3H_7)_4N]OH$ and either $NaAlO_2$, or $Fe(NO_3)_3$, or $Ga(NO_3)_3$ in water for six hours at 150° C. in an autoclave under autogenous pressure. After the reaction mixtures had cooled down, the silicates formed were filtered off, washed with water until the pH of the wash water was about 8, dried a 120° C. and calcined at 500° C. The silicates A-C had the following properties:

(a) thermally stable up to a temperature above 800° C., (b) an X-ray powder diffraction pattern substantially equal to the one given in Table B, (c) a value for m as mentioned below:
silicate A: $Al_2O_3/SiO_2$ molar ratio = 0.0133,
silicate B: $Fe_2O_3/SiO_2$ molar ratio = 0.0050,
silicate C: $Ga_2O_3/SiO_2$ molar ratio = 0.0083.

The molar composition of the aqueous mixtures from which the silicates A-C were prepared can be represented as follows:

Silicate A:
1 $Na_2O$. 4.5$[(C_3H_7)_4N]_2O$. 0.33 $Al_2O_3$. 25 $SiO_2$. 450 $H_2O$ Silicate B:
1 $Na_2O$. 1.5$[(C_3H_7)_4N]_2O$. 0.125 $Fe_2O_3$. 25 $SiO_2$. 468 $H_2O$ Silicate C:
1 $Na_2O$. 4.5$[(C_3H_7)_4N]_2O$ + 0.22 $Ga_2O_3$. 25 $SiO_2$. 25 $SiO_2$. 450 $H_2O$.

The silicates D-F were prepared from the silicates A-C, respectively, by boiling the silicates A-C with 1.0 molar $NH_4NO_3$ solution, washing with water, boiling again with 1.0 molar $NH_4NO_3$ solution and washing, drying and calcining. A catalyst 5 was prepared from silicate D by impregnating silicate D with an aqueous solution of a manganese salt followed by drying the composition and calcining it. Catalyst 5 contained 3%w manganese. Silicates E and F were used as such as catalyst 6 and catalyst 7, respectively.

CATALYST MIXTURES I–V

Five catalyst mixtures were prepared. The catalyst mixtures I–IV consisted of each of a physical mixture of two of the above-mentioned catalysts in the following ratio:

Cat. mixture I = 2 pbv of cat. 4 + 1 pbv of cat. 5,
Cat. mixture II = 2 pbv of cat. 4 + 1 pbv of cat. 6,
Cat. mixture III = 2 pbv of cat. 4 + 1 pbv of cat. 7,
Cat. mixture IV = 2.5 pbv of cat. 2 + 1 pbv of cat. 5.
Catalyst mixture V consisted of a layer of catalyst 3 and a layer of catalyst 1 in a volume ratio of 1:2.

The catalyst mixtures I–V and catalyst 1 were tested for the preparation in one or two steps of a hydrocarbon mixture from an $H_2/CO$ mixture. The test was carried out in one or two reactors of 50 ml each, in which a fixed catalyst bed having a volume of 7.5 ml was present. Ten experiments were carried out. The experiments 1 and 3–5 were carried out in one step; the other experiments in two steps. In all the experiments, with the exception of experiment 10, a temperature of 375° C. was used in the first step. In experiment 10 the temperature in the first step was 280° C. In all the experiments carried out in two steps the temperature in the second step was 220° C. In all the experiments, with the exception of experiment 10, a pressure of 60 bar was used. In experiment 10 the pressure was 30 bar. In all the experiments the space velocity, based on the sum of the total catalyst system (in the first + if used, the second step) was a 500 Nl/l catalyst/h. In the experiments 6–8 the $C_4^-$ fraction of the product from the first step was used as the feed for the second step. In the experiments 2, 9 and 10 the total reaction product from the first step was used as the feed for the second step.

The results of the experiments are listed in Table C. The amount of water added in the experiments 3–9 is expressed in ml water/l total catalyst system (in the first + if used, the second step)/h.

TABLE C

| Experiment No. | 1 | 2 | 3 | 4 | 5 | 6 | 7 | 8 | 9 | 10 |
|---|---|---|---|---|---|---|---|---|---|---|

Cat. mixture in

TABLE C-continued

| Experiment No. | 1 | 2 | 3 | 4 | 5 | 6 | 7 | 8 | 9 | 10 |
|---|---|---|---|---|---|---|---|---|---|---|
| the first step, No. | I | I | I | II | III | I | II | III | I | IV |
| $H_2/CO$ molar ratio of the feed for the first step | 0.8 | 0.8 | 0.45 | 0.45 | 0.45 | 0.45 | 0.45 | 0.45 | 0.45 | 0.9 |
| Amount of water added to the feed for the first step, $ml \cdot l^{-1} \cdot h^{-1}$ | — | — | 115 | 115 | 115 | 115 | 115 | 115 | 15 | — |
| $H_2/CO$ molar ratio of the product from the first step | 1.7 | 1.7 | 2.0 | 1.9 | 2.1 | 2.0 | 1.9 | 2.1 | 0.5 | 1.8 |
| Cat. or cat. mixture in the second step, No. | — | 1 | — | — | — | 1 | 1 | 1 | V | 1 |
| Amount of water added to the feed for the second step, $ml \cdot l^{-1} \cdot h^{-1}$ | — | — | — | — | — | — | — | — | 100 | — |
| Conversion of the synthesis gas, % | 62 | 94 | 53 | 49 | 55 | 98 | 97 | 98 | 98 | 95 |
| Composition of the reaction product, % w | | | | | | | | | | |
| $C_4^-$ | 40 | 45 | 37 | 29 | 26 | 36 | 35 | 34 | 29 | 50 |
| $C_5-C_{12}$ | 57 | 38 | 58 | 69 | 70 | 31 | 32 | 33 | 49 | 35 |
| $C_{13}-C_{19}$ | 3 | 7 | 5 | 2 | 4 | 13 | 13 | 13 | 10 | 6 |
| $C_{20}^+$ | — | 10 | — | — | — | 20 | 20 | 20 | 12 | 9 |

Of the experiments listed in the table, only the two-step experiments 2 and 6–10 are experiments according to the invention. The one-step experiments 1 and 3–5 are outside the scope of the invention. They have been included in the patent application for comparison.

The advantages of the two-step process now proposed as regards the conversion of the $H_2/CO$ mixture and the composition of the reaction product are evident when the results are compared of the experiments 1 and 2, of the experiments 3 and 9, and of the experiments 3–5 and, respectively, 6–8. In the experiments 3 and 9 the total amount of water added was equal.

What is claimed is:

1. A process for the preparation of a hydrocarbon mixture, from a feed mixture of carbon monoxide and hydrogen with an $H_2/CO$ molar ratio of less than 1.0 which comprises contacting said feed at a temperature of 200°–500° C., a pressure of 1–150 bar and a space velocity of 50–5000 Nl gas/l catalyst/h in a first contact zone with a trifunctional catalyst combination containing: (a) at least one metal component with catalytic activity for the conversion of an $H_2/CO$ mixture into acyclic hydrocarbons and/or acyclic oxygen-containing hydrocarbons, (b) at least one metal component with catalytic activity for the conversion of an $H_2O/CO$ mixture into an $H_2/CO_2$ mixture, and (c) a crystalline silicate with catalytic activity for the conversion of acyclic hydrocarbons and acyclic oxygen-containing hydrocarbons into aromatic hydrocarbons, which silicate has the following properties:
   (a) thermally stable up to a temperature above 600° C.,
   (b) an X-ray powder diffraction pattern showing, inter alia, the reflections given in Table A of the specification,
   (c) a composition which includes oxides of hydrogen, alkali metal and/or alkaline-earth metal and silicon, and at least one oxide of a trivalent metal, A, selected from the group formed by aluminum, iron and gallium, wherein $A_2O_3/SiO_2$ molar ratio(m) is less than 0.1; and
   contacting at least the $C_2^-$ fraction of the reaction product from the first contact zone in a second contact zone at a temperature of 125°–350° C. and a pressure of 1–150 bar with a catalyst containing at least one metal component with catalytic activity for the conversion of an $H_2/CO$ mixture into acyclic hydrocarbons, which metal components have been selected from the group formed by cobalt, nickel and ruthenium, with the proviso that (a) if the feed to the second contact zone has an $H_2/CO$ molar ratio of less than 1.5, water is added to this feed in an amount determined by the $H_2/CO$ molar ratio of the feed for the first step, the activity of the catalyst combination in said first step for converting an $H_2O/CO$ mixture into an $H_2/CO$ mixture and the desired $H_2/CO$ molar ratio of the first step reaction product, and (b) that said catalyst is a bifunctional combination which also contains at least one metal component with catalytic activity for the conversion of an $H_2O/CO$ mixture into an $H_2/CO_2$ mixture.

2. A process according to claim 1, wherein the $H_2/CO$ mixture feed for the first step has an $H_2/CO$ molar ratio of more than 0.25 and has been obtained by steam gasification of a carbon-containing material at a temperature of 900°–1500° C. and a pressure of 10–100 bar.

3. A process according to claim 1, wherein the crystalline silicate contains only one trivalent metal A selected from aluminum, iron and gallium.

4. A process according to claim 1 characterized in that the crystalline silicate has a value for m which is greater than 0.002 but smaller than 0.05.

5. A process according to claim 4, wherein the crystalline silicate is an aluminum silicate which has a value for m which is greater than 0.005 and the silicate contains 0.1–10%w of manganese.

6. A process according to claim 1, wherein the trifunctional catalyst combination in the first contact zone is composed of two separate catalysts X and Y, of which catalyst X has the activity for the conversion of an $H_2/CO$ mixture into acyclic hydrocarbons and/or acyclic oxygen-containing hydrocarbons and activity for the conversion of an $H_2O/CO$ mixture into an $H_2/CO_2$ mixture and catalyst Y is the crystalline silicate.

7. A process according to claim 6, wherein the X-catalyst is a catalyst capable of converting an $H_2/CO$ mixture into substantially methanol and/or dimethyl ether.

8. A process according to claim 6, wherein the X-catalyst is a catalyst which contains 30–75 pbw iron and 5–40 pbw magnesium per 100 pbw alumina and which has been prepared by impregnating an alumina carrier with one or more aqueous solutions of salts of iron and of magnesium, followed by drying the composition, calcining it at a temperature of 700°–1200° C. and reducing it.

9. A process according to claim 6, wherein the X-catalyst is a catalyst which contains 10–40 pbw iron and 0.25–10 pbw chromium per 100 pbw silica and which has been prepared by impregnating a silica carrier with one or more aqueous solutions of salts of iron and chromium, followed by drying the composition, calcining it, and reducing it at a temperature of 350°–750° C.

10. A process according to claim 1, wherein in the first contact zone the trifunctional catalyst combination is composed of three separate catalysts X, Y and Z, of which catalyst X has the activity for the conversion of an $H_2/CO$ mixture into acyclic hydrocarbons, catalyst Z has the activity for the conversion of an $H_2O/CO$ mixture into an $H_2/CO_2$ mixture and catalyst Y is the crystalline silicate.

11. A process according to claim 1, wherein water is added to the feed to the first contact zone in an amount sufficient to ensure that the reaction product has an $H_2/CO$ molar ratio of at least 1.5.

12. A process according to claim 1, wherein the catalyst in the second zone contains 10–40 pbw cobalt and 0.25–5 pbw zirconium, titanium or chromium per 100 pbw silica and which catalyst has been prepared by impregnating a silica carrier with one or more aqueous solutions of salts of cobalt and zirconium, titanium or chromium, followed by drying the composition, calcining it at 350°–700° C. and reducing it at 200°–350° C.

13. A process according to claim 1, wherein water is added to the feed for the second contact zone and the bifunctional catalyst in said contact zone is composed of two separate catalysts A and B, of which catalyst A has the activity for the conversion of an $H_2/CO$ mixture into acyclic hydrocarbons and catalyst B has the activity for the conversion of an $H_2O/CO$ mixture into an $H_2/CO_2$ mixture.

14. A process according to claim 13, wherein the bifunctional catalyst combination contains as catalyst A a cobalt catalyst as described in claim 13 and as catalyst B a CuO-ZnO composition.

15. A process according to claim 13 or claim 14 wherein said second contact zone comprises a fixed catalyst bed built up of two or more alternate layers of particles of catalyst B and catalyst A.

* * * * *